United States Patent [19]
Hall-Goulle

[11] Patent Number: 6,071,632
[45] Date of Patent: Jun. 6, 2000

[54] TRIBOLUMINESCENT LANTHANIDE[III] COMPLEXES

[75] Inventor: Véronique Hall-Goulle, Bern, Switzerland

[73] Assignee: Ciba Specialty Chemicals Corporation, Tarrytown, N.Y.

[21] Appl. No.: 08/860,597

[22] PCT Filed: Jan. 3, 1996

[86] PCT No.: PCT/EP96/00005

§ 371 Date: Jul. 2, 1997

§ 102(e) Date: Jul. 2, 1997

[87] PCT Pub. No.: WO96/20942

PCT Pub. Date: Jul. 11, 1996

[30] Foreign Application Priority Data

Jan. 6, 1995 [CH] Switzerland .................. 40/95

[51] Int. Cl.[7] .............. B32B 9/00; C09K 11/02; C07D 231/00
[52] U.S. Cl. .............. 428/690; 252/301.16; 252/301.35; 534/15; 546/6; 548/106
[58] Field of Search .................. 428/690, 917; 252/301.16, 301.35; 534/15; 546/6; 548/106

[56] References Cited

U.S. PATENT DOCUMENTS

| | | | |
|---|---|---|---|
| 3,398,099 | 8/1968 | Kleinerman | 252/301.2 |
| 4,761,481 | 8/1988 | Hale et al. | 546/296 |
| 4,920,195 | 4/1990 | Kankare et al. | 534/16 |
| 5,504,195 | 4/1996 | Leedham et al. | 534/15 |
| 5,854,008 | 12/1998 | Diamandis | 435/7.91 |

FOREIGN PATENT DOCUMENTS 0259951  3/1988  European Pat. Off. .

OTHER PUBLICATIONS

Advances in Physics, 1977, vol. 26, No. 6, 887–948 "Triboluminescence" Allen Walton.

Inorganic Syntheses, 11, 1968, 94 "Volatile Rare–Earth Cholates of 2,2,6,6–Tetramethylheptane–3,5–dione" Kent Eisentraut.

Chemie—Ing.—Techn. 38, 3 (1966) 331–342 "Zerkleinerungsuntersuchungen mit tribolumineszierenden Stoffen" Kurten.

*Primary Examiner*—Paul Thibodeau
*Assistant Examiner*—Kevin R. Kruer
*Attorney, Agent, or Firm*—Kevin T. Mansfield; David R. Crichton

[57] ABSTRACT

In one of its aspects, the invention relates to compounds of formula I

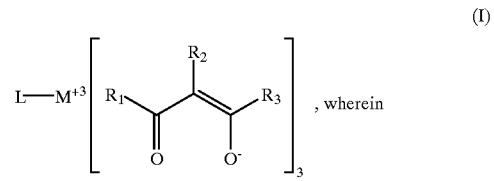

M is Eu, Tb or Dy, Sm;

$R_2$ is hydrogen or $C_1$–$C_6$alkyl, and $R_1$ and $R_3$ are each independently of the other phenyl, hydrogen or $C_1$–$C_6$alkyl, and L is p-N,N-dimethylaminopyridine, N-methylimidazole or p-methoxypyridine-N-oxide.

The invention also relates to the use of these compounds for optical sensors sensitive to impact, tension or pressure.

15 Claims, No Drawings

TRIBOLUMINESCENT LANTHANIDE[III] COMPLEXES

This application is a national stage application filed under 35 USC 37 of PCT/EP96/00005.

BACKGROUND OF THE INVENTION

The present invention relates to lanthanide[III] complexes of 1,3-diketones, which complexes have a high luminescence quantum yield as well as long-lasting luminescence, a narrowband emission spectrum and bright triboluminescence. The invention also relates to the use of said compounds for optical sensors sensitive to impact, tension or pressure.

The phenomenon of triboluminescence (emission of light under strong mechanical stress) has long been known and is described, inter alia, in Advances in Physics 1977, Vol. 26, No. 6, 887–948 or in Math. Naturwiss. Unterricht 45/4, 1992, 195–202. A great number of crystalline compounds display this phenomenon, but as yet only very few are known whose emission is so strong as to be easily observable also in daylight. The brightest triboluminescent substance known so far is triethylammonium tetrakis(dibenzoylmethanato)europate(III).

Although the phenomenon of triboluminescence is well known, its cause cannot be completely accounted for yet and hence no predictions can be made concerning the occurrence of particularly intense triboluminescent compounds.

Specific Eu(III) complexes with pyridine-N-oxide, 2-, 3-, or 4-picoline-N-oxide and bipyridine-N,N-dioxide as well as thenoyltrifluoroacetone as ligand are disclosed in CA 114 (18):177114p as triboluminescent substances of intense brightness.

BRIEF SUMMARY OF THE INVENTION

It has now been found that a specific group of predominantly colourless lanthanide complexes displays particularly bright triboluminescence, which complexes have very narrowband emission lines, pronounced Stokes' shift, as well as long-lasting luminescence and a high quantum yield of photochemically excited luminenscence.

By virtue of their long-lasting photochemically excited luminescence and high luminescence quantum yield, these compounds are also particularly suitable for use as pigments or dyes in the field of security printing. Bank notes and securities are typical examples requiring a high degree of security against unauthorised duplication. The high luminescence of the compounds is able to induce colour changes in the documents printed therewith when duplicated in conventional manner, so that the documents are identifiable as duplicates.

DETAILED DESCRIPTION OF THE INVENTION

In one of its aspects, the invention relates to compounds of formula I

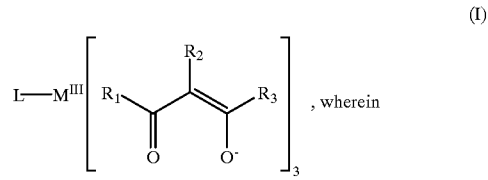

, wherein

M is Eu, Tb or Dy, Sm;
$R_2$ is hydrogen or $C_1$–$C_6$alkyl, and
$R_1$ and $R_3$ are each independently of the other phenyl, hydrogen or $C_1$–$C_6$alkyl, and
L is p-N,N-dimethylaminopyridine, N-methylimidazole or p-methoxypyridine-N-oxide.

The $C_1$–$C_6$alkyl groups can be straight-chain or branched and are typically methyl, ethyl, n-propyl, isopropyl, n-butyl, sec-butyl, isobutyl, tert-butyl or the different positional isomers of pentyl and hexyl. The alkyl groups preferably contain 3–5 carbon atoms.

M is preferably Eu, Tb or Dy.
$R_2$ is preferably hydrogen.
Most preferably, $R_1$ and $R_3$ are each tert-butyl or phenyl.

The invention also relates to a process for the preparation of compounds of formula I, which comprises reacting compounds of formula II

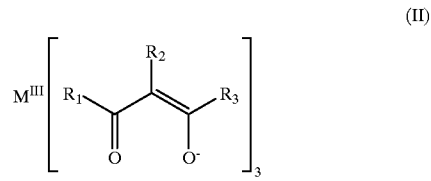

in an organic solvent with p-N,N-dimethylaminopyridine, N-methylimidazole or p-methoxy-pyridine-N-oxide, wherein $R_1$, $R_2$, $R_3$ and M have the meaning given above.

The preparation of the compounds of formula II is known per se and is described in K. J. Eisentraut, R. E. Sievers, Inorg. Syn. 11, 1968, 94.

Organic solvents are preferably alcohols, ethers, ketones, acid amides, aliphatic or aromatic nitriles, saturated or unsaturated hydrocarbons, chlorinated hydrocarbons or aromatic compounds, or mixtures thereof.

Particularly preferred solvents are $C_1$–$C_6$alcohol, benzonitrile or acetonitrile.

The reaction is preferably carried out in the temperature range from 20° C. to 150° C.

Reaction time and printing conditions are per se non-critical, and the reaction is preferably carried out under conditions of normal pressure. The reaction time may be in the range from 10 minutes to 24 hours and is preferably from 1 to 5 hours.

By virtue of their luminescent properties, the compounds can be used as optical sensors for detecting oxygen, as is disclosed in the case of some lanthanide complexes, inter alia, in EP-A-0 259 951.

Another potential field of use for triboluminescent lanthanide complexes is also, for example, that of surface analysis in grinding processes in spiral jet mills, as described by H. Kürten and G. Rumpf in Chem. Ing. Technik 38, 3 (1966) 331–342.

Their triboluminescent properties make the compounds of formula I admirably suited for use as optical sensors sensitive to impact, tension or pressure, which sensors can, for example, be attached as warning elements to cargo which has to be protected from too great a mechanical stress.

Accordingly, the invention also relates to a coated material sensitive to impact, tension or pressure, wherein a crystalline layer a) consisting of the compounds of formula I is coated onto at least one side of a substrate.

The form of the substrate is intrinsically non-critical and will depend on the requirements of the user. Possible embodiments are, for example, spherical, cylindrical, u-shaped or planar.

The substrate is preferably substantially planar.

The substrate can be coated with the crystalline layer a) on one side or on both sides, but preferably on one side only.

The compounds of formula I can also be homogeneously dispersed in crystalline form in polymers in which they do not dissolve.

Suitable polymers are, for example, thermoplastic polymers, typically polyolefins, polyesters or polyamides. However, it is also possible to use crosslinked polymers, typically heat-curable melamine resins, as well as acrylates and polyesters which are crosslinked with melamine resins; epoxy resins or polyurethanes. Radiation-curable polymers, typically unsaturated polyesters or acrylate-functional prepolymers, can also be used.

A preferred embodiment of the invention is that wherein the compounds of formula I are homogeneously dispersed in a polymeric material and the substrate is coated with said polymeric material.

If the crystalline layer a) is first applied to the substrate, then in a preferred embodiment of the invention a polymeric protective layer is additionally coated onto said crystalline layer a).

Another preferred embodiment of the invention consists of a substrate coated on at least one side with an adhesive layer to which the crystalline layer a) is applied. In this case, too, a polymeric protective layer can, if required, be additionally applied.

The substrate can consist of any material. It may consist of metal, plastic, a mineral or a semi-conductor.

The substrate is preferably a plastic material.

The substrate is preferably flexible.

The invention also relates to the use of compounds of formula I in optical sensors which are sensitive to impact, tension or pressure.

The following Examples illustrate the invention.

Working Examples

Example A1

Preparation of a tris(1,3 di-tert-butyl-β-propanedione)europate-p-dimethyl-aminopyridine complex 5 ml of a 5 mmolar ethanolic solution of p-dimethylaminopyridine are slowly added to 50 ml of a 5 mmolar solution of tris(1,3 di-tert-butyl-β-propanedione)europate in ethanol. The turbid solution is refluxed for 2.5 hours. After cooling, the solution is filtered over kieselgur and the filtrate is fully concentrated by evaporation to dryness. The crude product is recrystallised from acetonitrile (only the complex containing p-methoxypyridine-N-oxide is recrystallised from petroleum ether). The tris(1,3 di-tert-butyl-β-propanedione)europate-p-dimethylaminopyridine complex is obtained in good yield. The compounds A2–A6 characterised in Table 1 are prepared in analogous manner.

TABLE 1

| No. | M | $R_2$ | $R_1$ | $R_3$ | L | % C (th.) | % H (th.) | % N (th.) | % C (exp.) | % H (exp.) | % N (exp.) | m.p. (°C.) | Colour |
|---|---|---|---|---|---|---|---|---|---|---|---|---|---|
| A1 | Tb | H | t-bu | t-bu | 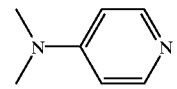 | 57.84 | 8.07 | 3.37 | 57.57 | 8.11 | 3.15 | 150.8 | white |
| A2 | Dy | H | t-bu | t-bu | 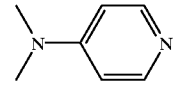 | 57.63 | 8.10 | 3.36 | 57.56 | 8.10 | 3.33 | 150.1 | white |
| A3 | Eu | H | t-bu | t-bu | 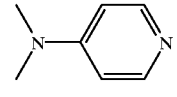 | 58.29 | 8.14 | 3.40 | 58.22 | 8.16 | 3.30 | 148.1 | white |
| A4 | Tb | H | t-bu | t-bu | 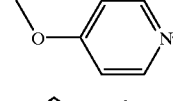 | 56.19 | 7.68 | 1.68 | 56.16 | 7.82 | 1.70 | 128.5 | white |
| A5 | Tb | H | t-bu | t-bu | 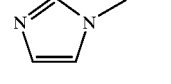 | 56.22 | 8.03 | 3.54 | 55.98 | 7.99 | 3.66 | 168.0 | white |
| A6 | Eu | H | phenyl | phenyl | 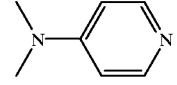 | 66.16 | 4.59 | 2.96 | 66.08 | 4.89 | 3.25 | 165.4 | yellowish orange | th. = theoretical value
exp. = experimentally obtained value
m.p. = melting point

Use Examples

Example B1

0.6 g of the compound of Example A1 is stirred into a mixture consisting of 4.43 g of polyisocyanate (Desmodur® N 75, supplied by Bayer AG) and 5.54 g of polyol (Desmophen® 650, supplied by Bayer AG) until the mixture is homogeneous. A 2 mm metal plate is coated with this mixture over a surface area of c. 50 cm². The layer is dried for 30 minutes at 80° C. to form a hard polyurethane layer. The thickness of the dry layer is c. 500 μm. Irradiation of this layer with light having a wavelength of 365 nm results in bright green luminescence. Bright green luminescence is also visible when the surface is subjected to pressure, impact or friction.

Example B2

0.6 g of the compound of Example A1 is stirred into 10 g of a commercial adhesive (Konstruvit, supplied by Geistlich AG) until the mixture is homogeneous. The mixture is then coated onto a plastic card over a surface area of c. 20 cm² and allowed to dry. Irradiation of this adhesive layer with light having a wavelength of 365 nm results in bright green luminescence. Bright green luminescence is also visible when the surface is subjected to pressure, impact or friction.

Example B3

0.7 g of the compound of Example A1 are stirred into 7.4 g of a rubber adhesive (Sanford rubber cement) until the mixture is homogeneous. The mixture is then coated onto a plastic card over a surface area of c. 20 cm² and allowed to dry. Bright green luminescence is visible when the surface is subjected to pressure, impact or friction. Irradiation of this adhesive layer with light having a wavelength of 365 nm results in bright green luminescence.

What is claimed is:

1. A compound of formula I

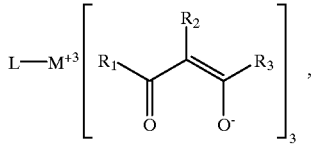

(I)

wherein

M is Eu, Tb, Dy or Sm;

$R_2$ is hydrogen or $C_1$–$C_6$alkyl, and $R_1$ and $R_3$ are each independently of the other phenyl, hydrogen or $C_1$–$C_6$alkyl, and L is p-N,N-dimethylaminopyridine, n-methylimidazole or p-methoxypyridine-n-oxide.

2. A compound according to claim 1, wherein M is Eu, Tb or Dy.

3. A compound according to claim 1, wherein $R_2$ is hydrogen.

4. A compound according to claim 1, wherein both $R_1$ and $R_3$ are phenyl or tert-butyl.

5. A coated material comprising a crystalline layer, wherein said crystalline layer comprising the compound of formula I according to claim 1 is coated onto at least one side of a substrate.

6. A coated material according to claim 5, wherein the substrate is substantially planar.

7. A coated material according to claim 5, wherein a polymeric protective layer is coated onto the crystalline layer a).

8. A coated material according to claim 5, wherein the crystalline layer consists of a polymeric material having the compound of formula I dispersed therein.

9. A coated material according to claim 5, wherein the substrate is coated on at least one side with an adhesive layer to which the crystalline layer is applied.

10. A coated material according to claim 5, wherein the substrate is a plastic material.

11. A process for the preparation of a compound according to claim 1, which comprises reacting in an organic solvent a compound of formula II

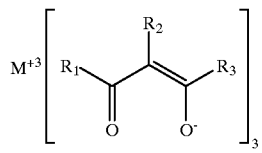

(II)

in an organic solvent with p-N,N-dimethylaminopyridine, N-methylimidazole or p-methoxypyridine-N-oxide, wherein M is Eu, Tb, Dy or Sm;

$R_2$, is hydrogen or $C_1$–$C_6$alkyl, and $R_1$ and $R_3$ are each independently of the other phenyl, hydrogen or $C_1$–$C_6$alkyl.

12. A process according to claim 11, wherein the organic solvent is selected from the group consisting of alcohols, ethers, ketones, acid amides, aliphatic and aromatic nitriles, saturated and unsaturated hydrocarbons, chlorinated hydrocarbons and aromatic compounds, and mixtures thereof.

13. A process according to claim 12, wherein the organic solvent is a $C_1$–$C_6$alcohol, benzonitrile, or acetonitrile.

14. A process according to claim 11, which comprises carrying out the reaction in the temperature range from 20° C. to 150° C.

15. A method for producing an optical sensor comprising applying a coating material containing a compound according to claim 1 onto a substrate, wherein the resulting coated substrate exhibits luminescence when subjected to pressure, impact, or friction.

* * * * *